US011853707B1

(12) United States Patent
McNair

(10) Patent No.: US 11,853,707 B1
(45) Date of Patent: *Dec. 26, 2023

(54) DETERMINING ADEQUACY OF DOCUMENTATION USING PERPLEXITY AND PROBABILISTIC COHERENCE

(71) Applicant: CERNER INNOVATION, INC., Kansas City, KS (US)

(72) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 127 days.

This patent is subject to a terminal disclaimer.

(21) Appl. No.: 17/500,372

(22) Filed: Oct. 13, 2021

Related U.S. Application Data

(63) Continuation of application No. 16/574,735, filed on Sep. 18, 2019, now Pat. No. 11,188,717, which is a continuation of application No. 15/854,610, filed on Dec. 26, 2017, now Pat. No. 10,460,035.

(60) Provisional application No. 62/439,151, filed on Dec. 26, 2016.

(51) Int. Cl.
  *G10L 15/00* (2013.01)
  *G06F 40/30* (2020.01)
  *G16H 10/60* (2018.01)

(52) U.S. Cl.
  CPC ............. *G06F 40/30* (2020.01); *G16H 10/60* (2018.01)

(58) Field of Classification Search
  CPC ...... G06F 40/20; G06F 40/174; G06F 40/279; G10L 15/26
  See application file for complete search history.

(56) References Cited

U.S. PATENT DOCUMENTS

| | | | |
|---|---|---|---|
| 5,943,443 A | 8/1999 | Itonori et al. | |
| 6,178,420 B1 | 1/2001 | Sassano | |
| 6,850,937 B1 | 2/2005 | Hisamitsu et al. | |
| 7,200,802 B2 | 4/2007 | Kawatani | |
| 7,516,070 B2* | 4/2009 | Kahn | G06F 40/174 704/277 |
| 10,423,721 B2* | 9/2019 | Zimmerman | G06F 40/186 |
| 10,460,035 B1 | 10/2019 | Mcnair | |
| 11,188,717 B1 | 11/2021 | Mcnair | |
| 2003/0099379 A1* | 5/2003 | Monk | G06V 30/40 382/218 |

(Continued)

*Primary Examiner* — Daniel Abebe
(74) *Attorney, Agent, or Firm* — Kilpatrick Townsend & Stockton LLP

(57) ABSTRACT

Technologies are provided for determining deficiencies in narrative textual data that may impact decision-making in a decisional context. A candidate text document and a reference corpus of text may be utilized to generate one or more topic models and document-term matrices, and then to determine a corresponding statistical perplexity and probabilistic coherence. Statistical determinations of a degree to which the candidate deviates from the reference normative corpus are determined, in terms of the statistical perplexity and probabilistic coherence of the candidate as compared to the reference. If the difference is statistically significant, a message may be reported to user, such as the author or an auditor of the candidate text document, so that the user has the opportunity to amend the candidate document so as to improve its adequacy for the decisional purposes in the context at hand.

20 Claims, 16 Drawing Sheets

(56) References Cited

U.S. PATENT DOCUMENTS

| | | | |
|---|---|---|---|
| 2006/0167686 A1* | 7/2006 | Kahn | G06F 40/174 |
| | | | 704/E15.044 |
| 2007/0299664 A1* | 12/2007 | Peters | G06F 40/16 |
| | | | 704/235 |
| 2012/0072859 A1 | 3/2012 | Wang et al. | |
| 2013/0021344 A1* | 1/2013 | Wang | G06V 30/40 |
| | | | 345/581 |
| 2017/0322930 A1 | 11/2017 | Drew | |
| 2018/0300315 A1 | 10/2018 | Leal et al. | |
| 2020/0193153 A1 | 6/2020 | Lee et al. | |

* cited by examiner

EXAMPLE: CENTRAL-LINE-ASSOCIATED BLOOD STREAM INFECTION (CLABSI)

On Day 1 the patient was admitted to ICU – with central line and Foley catheter in place. On Day 5 they're doing a lot better. They've been read – weaned from that ventilator and the Central line and Foley catheter are removed. On Day 6 they are doing well and transfer to the Orthopedic unit. T
and there are no co
cultures, blood cul
the fifth, the chest
Then we will go to
If anything, the org On the second day they still have their subclavian line and there are no other symptoms. On Day 3 they have the Foley catheter and now they have a fever of 38.2. On Day 4 they are afebrile but on day 5 they have a urine culture or urinalysis done that is positive.

The patient remains afebrile, and you can see on Day 3 and 5 that we have an element of criterion for one of the CLABSI definitions. A fever and a positive culture and they have a gap day in between with no symptoms. On Day 6 the patient remained afebrile but on Day 7 they have the Foley taken out and they are afebrile and the urine culture was collected and now they have 10,000 colonies units of E. coli. On this you can see the second set of blood cultures. They had abnormal urine on Day 5 and on Day 7 they had a positive culture. This means…

This patient did hav
confirmed bloodstre
the same day as her
BSI because her cat
same day. The reaso
it was her only sym
patient that does no
there is a catheter –
65 – the correct ter
of age in order for y
because the patient did have fever and that counts regardless of age in the definition…

FIG. 4.

EXAMPLE: NON-ST-ELEVATED MYOCARDIAL INFARCTION (NSTEMI)

The patient, a 65 years old male, reports that he had chest pain

The patient complains of chest pain. He has a heart attack, I am sure of this.

He reports that he felt sweaty during the pain. He did not want to bother anyone so he rested and the pain eased. He reports that it was very painful, radiating to left arm and jaw. He is currently not in any pain, although he feels quite tired. He has been a smoker for 40 years. On average, he has around 10 cigarettes a day. He has no past medical history of chest pain, ischemic heart disease or heart failure. ECG not back yet....

Dr. X requested evaluation... Inferior wall MI ... surgery. Inferior wall MI ... complete resolution of his ... activity includes walking, ... history of cerebrovascular ... history of essential hypertension and was prescribed metoprolol succinate once daily by PCP, but patient is not taking as he cannot afford it. Exam: Patient is an 81 year old male in no acute distress. Height and weight are appropriate for age. Vitals taken; BP 157/92. Chest is clear. Physical exam is unremarkable. No pedal edema. EKG shows nonspecific T-wave changes, consistent with remote AMI in distant past. Negative troponins x3. Labs show creatinine at 1.5, a slight increase from his baseline and possibly indicating early renal insufficiency. Will have PCP monitor BUN & Creatinine for renal function and nephrology referral if necessary. HTN is likely due to patient's noncompliance with existing metoprolol rx. Will coordinate with Dr. X as unclear if he was aware of financial situation. Change to propranolol 20 mg, 2 tab PO daily, first dose administered in office. Provided 30-day supply of free propranolol samples. Reevaluate HTN in 3 days...

FIG. 5.

```
##########################################################################

#   Clinical documentation quality - Gibbs LDA topic modeling with Kendall tau distance
#   metric of matched probabilistic coherence vectors

#################################################################### https://github.com/dselivanov/text2vec
https://cran.r-project.org/web/packages/text2vec/index.html
library(text2vec)

library(Matrix)
library(NLP)
library(lda)
library(parallel)
library(topicmodels)
library(tm)
library(SnowballC)
library(textmineR)

# enable parallel processing
detectCores()

# coherence fun; M is nbr of stemmed words to use in determination
prob_coherence <- function (phi, dtm, M=5) {
  # error trapping
  if (!is.numeric(phi)) {
    stop("phi must be a numeric matrix whose rows index topics and columns\n",
      " index terms or phi must be a numeric vector whose entries index terms.")
  }
  if (!is.matrix(dtm) & !class(dtm) %in% c("dgCMatrix", "dgTMatrix", "dgeMatrix", "dgRMatrix")) {
    stop("dtm must be a matrix. This can be a standard dense matrix or a\n",
      " sparse matrix of class dgCMatrix, dgTMatrix, dgRMatrix, or dgeMatrix")
  }
  if (!is.numeric(M) | M < 1) {
    stop("M must be an integer in 1:ncol(phi) or 1:length(phi)")
  }
  if (is.null(colnames(dtm))) {
    stop("dtm must have colnames")
  }
  if (!is.matrix(phi)) {
    if (sum(names(phi)[1:M] %in% colnames(dtm)) != length(1:M)) {
      stop("names(phi)[1:M] are not in colnames(dtm)")
    }
  } else if (sum(colnames(phi)[1:M] %in% colnames(dtm)) != length(1:M)) {
    stop("colnames(phi)[1:M] are not in colnames(dtm)")
  }
```

.
.
.

CONTINUES IN FIG. 6B

*FIG. 6A*

CONTINUES FROM FIG. 6A

```
# probabilistic coherence fun def
  pcoh <- function(topic, dtm, M) {
    terms <- names(topic)[order(topic, decreasing=TRUE)][1:M]
    dtm.t <- dtm[, terms]
    dtm.t[dtm.t > 0] <- 1
    count.mat <- Matrix::t(dtm.t) %*% dtm.t
    num.docs <- nrow(dtm)
    p.mat <- count.mat/num.docs
    result <- sapply(1:(ncol(count.mat) - 1),
           function(x) {
             mean(p.mat[x, (x + 1):ncol(p.mat)]/p.mat[x, x] -
             Matrix::diag(p.mat)[(x + 1):ncol(p.mat)], na.rm=TRUE)
           }
    )
         mean(result, na.rm=TRUE)
  }
  # calculate probabilistic coherence
    if (!is.matrix(phi)) {
       return(pcoh(topic=phi, dtm=dtm, M=M))
    }
    apply(phi, 1,
       function(x) {
          pcoh(topic=x, dtm=dtm, M=M)
       }
    )
} inits
stpwd <- sort(unique(c(tm::stopwords("english"), tm::stopwords("SMART"))))
k <- 5
M <- 10
alph <- 0.1 ingest training data
train <- scan(file="c:/0_cerdsm/IP/clinical_documentation_quality/data/nstemi_train.txt",
         what="character", sep=",", quote="\"", dec=".", fill=FALSE, comment.char="")
train <- removeWords(train, stpwd)
lentrain <- length(train)

# create document-term matrix
train_dtm <- CreateDtm(doc_vec=train, doc_names=1:lentrain, stopword_vec=NULL,
          lower=TRUE, remove_punctuation=TRUE, remove_numbers=TRUE,
          stem_lemma_function=function(x) SnowballC::wordStem(x, "porter"))

# remove any rows in pre-processed dtm that have zero entries
rowTotals <- apply(train_dtm, 1, sum) # find the sum of words in each Document
train_dtm <- train_dtm[rowTotals > 0,]

# fit an LDA model to training data
train_model <- FitLdaModel(dtm=train_dtm, method="gibbs", k=k, iterations=1000, alpha=alph)
```

CONTINUES IN FIG. 6C

*FIG. 6B*

CONTINUES FROM FIG. 6B

```
# calc coherence within each of k topics; approximates semantic coherence or human
# understandability of a topic
coh0 <- prob_coherence(phi=train_model$phi,
              dtm=train_dtm, M=M)
round(coh0,3)
#  t_1   t_2   t_3   t_4   t_5
0.080 0.190 0.134 0.055 0.244 top words assoc with each topic in train
phi_train <- train_model[[2]]
vocab_train <- colnames(train_model[[2]])  # unlist(train_dtm@Dimnames[2])

topics_train <- list(rep("character",k))
for (i in 1:k) {
  words <- removeWords(names(sort(subset(phi_train[i,], phi_train[i,] > 1e-02), decreasing=TRUE)), stpwd)
  words <- subset(words, nchar(words) > 2)
  topics_train[[i]] <- words
} ingest test data
test1 <- scan(file="c:/0_cerdsm/IP/clinical_documentation_quality/data/nstemi_test1.txt",
        what="character", sep=",", quote="\"", dec=".", fill=FALSE, comment.char="")
lentest1 <- length(test1)

# create document-term matrix
test1_dtm <- CreateDtm(doc_vec=test1, doc_names=1:lentest1, stopword_vec=NULL,
          lower=TRUE, remove_punctuation=TRUE, remove_numbers=TRUE,
          stem_lemma_function=function(x) SnowballC::wordStem(x, "porter"))

# remove any rows in pre-processed dtm that have zero entries
rowTotals <- apply(test1_dtm, 1, sum) # find the sum of words in each Document
test1_dtm <- test1_dtm[rowTotals > 0,]

# fit an LDA model to test data
test1_model <- FitLdaModel(dtm=test1_dtm, method="gibbs", k=k, iterations=1000, alpha=alph)

# top words associated with each topic in test1
phi_test1 <- test1_model[[2]]
vocab_test1 <- colnames(test1_model[[2]])  # unlist(test1_dtm@Dimnames[2])

topics_test1 <- list(rep("character",k))
for (i in 1:k) {
  words <- removeWords(names(sort(subset(phi_test1[i,], phi_test1[i,] > 1e-02), decreasing=TRUE)), stpwd)
  words <- subset(words, nchar(words) > 2)
  topics_test1[[i]] <- words
}
```

CONTINUES IN FIG. 6D

*FIG. 6C*

CONTINUES FROM FIG. 6C

```
test1_match_train <- rep(0L, k)
for (i in 1:k) {
  ndx <- 0
  max_x <- 0
  for (j in 1:k) {
    x <- length(na.omit(match(as.vector(topics_test1[[j]]), as.vector(topics_train[[i]]))))
    if (x > max_x) {
      ndx <- j
      max_x <- x
    }
  }
  test1_match_train[i] <- ndx
}
test1_match_train
[1] 2 2 2 2 2 to calc coherence directly would re-cast test1_model$phi to align with train_model
setting colnames(phi) are not in colnames(dtm)

# calc coherence within each of k topics; approximates semantic coherence or human
# understandability of a topic
coh1 <- prob_coherence(phi=test1_model$phi,
            dtm=test1_dtm, M=M)
round(coh1,3)
#  t_1   t_2   t_3   t_4   t_5
0.111 0.051 0.115 0.098 0.194 coh_match <- coh1[test1_match_train] + rnorm(5, 0, 0.001)
names(coh_match) <- c("t_1","t_2","t_3","t_4","t_5")

# calculate Kendall tau correlation between test1 and train coherences on topics in test1 that
# match topics in train
kn <- cor.test(coh_match, coh0, method="kendall", exact=FALSE)
kn$p.value
# 0.142
abs(kn$estimate)
# 0.600  Kendall tau corr
# adequately coherent
suggest adequate coherence match if p.value < 0.20 or abs(tau) > 0.30 alternatively, may use paired Wilcoxon test
wilcox.test(coh_match, coh0, paired=TRUE, exact=TRUE)
wilcox.exact(coh_match, coh0, paired=TRUE, exact=TRUE)
ansari.tesr(coh_match, coh0, exact=TRUE)
perm.test(coh_match, coh0, paired=TRUE, exact=TRUE)
```

FIG. 6D

```
##################################################################

#   Clinical documentation quality - VEM LDA topic modeling with Welch t-test of perplx metric

############################################################ library(Matrix)
library(NLP)
library(lda)
library(parallel)
library(tm)
library(stringr)
library(SnowballC)
library(topicmodels)

# enable parallel
detectCores()

# inits
stpwd <- sort(unique(c(tm::stopwords("english"), tm::stopwords("SMART"))))
k <- 5
ctrl_dtm <- list(removePunctuation=TRUE, removeNumbers=TRUE,
         stemming=TRUE, wordLengths=c(3, Inf), stopwords=TRUE, weighting=function(x) weightTf(x))

# perplexity fun
perplx <- function(object, newdata, ...) {
  exp(-as.numeric(logLik(object, REML=TRUE))/object@n)
}

###############################################
# accept H0 for p > 0.0015
# alternative to Welch t-test
# mean(lda_perp_testx/lda_perp_train) > 1.5 or < 0.67
# perplx() allows to determine the perplx of a fitted model also for new data
# posterior() allows to obtain the topic distributions for documents and the term distributions for topics

###############################################
# load training data - NSTEMI
train <- data.frame(scan(file="c:/0_cerdsm/IP/clinical_documentation_quality/data/nstemi_train.txt",
what="character",
         sep=",", quote="\"", dec=".", fill=FALSE, comment.char="", allowEscapes=TRUE),
stringsAsFactors=FALSE)
lentrain <- length(train[,1])
train <- DataframeSource(train)

# construct corpora from data.frames
train.corpus <- Corpus(train)

# construct DTMs from corpora (preferably, a large plurality of documents that were deemed
# adequately complete and coherent; instead of single document example here)
train.dtm <- DocumentTermMatrix(train.corpus, control=ctrl_dtm)
```

CONTINUES IN FIG. 7B

*FIG. 7A*

CONTINUES FROM FIG. 7A

```
# remove any rows in pre-processed dtm that have zero entries
rowTotals <- apply(train.dtm , 1, sum) # find the sum of words in each Document
train.dtm <- train.dtm[rowTotals > 0,]

# construct LDA models
lda_train.1 <- LDA(train.dtm, method="VEM", control=list(alpha=0.1, seed=1231), k=k)
lda_train.2 <- LDA(train.dtm, method="VEM", control=list(alpha=0.1, seed=1232), k=k)

# determine perplx of training data
lda_perp_train.1 <- perplx(lda_train.1)
lda_perp_train.2 <- perplx(lda_train.2)
lda_perp_train <- c(lda_perp_train.1, lda_perp_train.2 + 0.1)
mean(lda_perp_train) # 104.1 process test1 data
test1 <- data.frame(scan(file="c:/0_cerdsm/IP/clinical_documentation_quality/data/nstemi_test1.txt",
what="character",
          sep=",", quote="\"", dec=".", fill=FALSE, comment.char="", allowEscapes=TRUE),
stringsAsFactors=FALSE)
lentest1 <- length(test1[,1])
test1 <- DataframeSource(test1)
test1.corpus <- Corpus(test1)
test1.dtm <- DocumentTermMatrix(test1.corpus, control=ctrl_dtm)
rowTotals <- apply(test1.dtm, 1, sum) # find the sum of words in each Document
test1.dtm <- test1.dtm[rowTotals > 0,]
lda_test1.1 <- LDA(test1.dtm, method="VEM", control=list(alpha=0.1, seed=1231), k=k)
lda_test1.2 <- LDA(test1.dtm, method="VEM", control=list(alpha=0.1, seed=1232), k=k)
lda_perp_test1.1 <- perplx(lda_test1.1)
lda_perp_test1.2 <- perplx(lda_test1.2)
lda_perp_test1 <- c(lda_perp_test1.1, lda_perp_test1.2 + 0.1)
mean(lda_perp_test1) # 48.3
# Welch t-test for difference in perplexities, test vs. train
p <- t.test(x=lda_perp_test1, y=lda_perp_train, alternative="two.sided")$p.value    # p=4.6e-03
p # reject H0 test2 <- data.frame(scan(file="c:/0_cerdsm/IP/clinical_documentation_quality/data/nstemi_test2.txt",
what="character",
          sep=",", quote="\"", dec=".", fill=FALSE, comment.char="", allowEscapes=TRUE),
stringsAsFactors=FALSE)
lentest2 <- length(test2[,1])
test2 <- DataframeSource(test2)
test2.corpus <- Corpus(test2)
test2.dtm <- DocumentTermMatrix(test2.corpus, control=ctrl_dtm)
rowTotals <- apply(test2.dtm, 1, sum) # find the sum of words in each Document
test2.dtm <- test2.dtm[rowTotals > 0,]
lda_test2.1 <- LDA(test2.dtm, method="VEM", control=list(alpha=0.1, seed=1231), k=k)
lda_test2.2 <- LDA(test2.dtm, method="VEM", control=list(alpha=0.1, seed=1232), k=k)
lda_perp_test2.1 <- perplx(lda_test2.1)
lda_perp_test2.2 <- perplx(lda_test2.2)
lda_perp_test2 <- c(lda_perp_test2.1, lda_perp_test2.2 + 0.1)
mean(lda_perp_test2) # 9.4
# Welch t-test for difference in perplexities, test vs. train
p <- t.test(x=lda_perp_test2, y=lda_perp_train, alternative="two.sided")$p.value    # p=5.9e-03
p # reject H0
```

CONTINUES IN FIG. 7C

*FIG. 7B*

CONTINUES FROM FIG. 7B

```r
test3 <- data.frame(scan(file="c:/0_cerdsm/IP/clinical_documentation_quality/data/nstemi_test3.txt",
what="character",
          sep=",", quote="\"", dec=".", fill=FALSE, comment.char="", allowEscapes=TRUE),
stringsAsFactors=FALSE)
lentest3 <- length(test3[,1])
test3 <- DataframeSource(test3)
test3.corpus <- Corpus(test3)
test3.dtm <- DocumentTermMatrix(test3.corpus, control=ctrl_dtm)
rowTotals <- apply(test3.dtm, 1, sum) # find the sum of words in each Document
test3.dtm <- test3.dtm[rowTotals > 0,]
lda_test3.1 <- LDA(test3.dtm, method="VEM", control=list(alpha=0.1, seed=1231), k=k)
lda_test3.2 <- LDA(test3.dtm, method="VEM", control=list(alpha=0.1, seed=1232), k=k)
lda_perp_test3.1 <- perplx(lda_test3.1)
lda_perp_test3.2 <- perplx(lda_test3.2)
lda_perp_test3 <- c(lda_perp_test3.1, lda_perp_test3.2 + 0.1)
mean(lda_perp_test3) # 17.2
# Welch t-test for difference in perplexities, test vs. train
p <- t.test(x=lda_perp_test3, y=lda_perp_train, alternative="two.sided")$p.value     # p=2.6e-04
p # reject H0 test4 <- data.frame(scan(file="c:/0_cerdsm/IP/clinical_documentation_quality/data/nstemi_test4.txt",
what="character",
          sep=",", quote="\"", dec=".", fill=FALSE, comment.char="", allowEscapes=TRUE),
stringsAsFactors=FALSE)
lentest4 <- length(test4[,1])
test4 <- DataframeSource(test4)
test4.corpus <- Corpus(test4)
test4.dtm <- DocumentTermMatrix(test4.corpus, control=ctrl_dtm)
rowTotals <- apply(test4.dtm, 1, sum) # find the sum of words in each Document
test4.dtm <- test4.dtm[rowTotals > 0,]
lda_test4.1 <- LDA(test4.dtm, method="VEM", control=list(alpha=0.1, seed=1231), k=k)
lda_test4.2 <- LDA(test4.dtm, method="VEM", control=list(alpha=0.1, seed=1232), k=k)
lda_perp_test4.1 <- perplx(lda_test4.1)
lda_perp_test4.2 <- perplx(lda_test4.2)
lda_perp_test4 <- c(lda_perp_test4.1, lda_perp_test4.2 + 0.1)
mean(lda_perp_test4) # 30.3
# Welch t-test for difference in perplexities, test vs. train
p <- t.test(x=lda_perp_test4, y=lda_perp_train, alternative="two.sided")$p.value     # p=3.6e-03
p # accept H0 test5 <- data.frame(scan(file="c:/0_cerdsm/IP/clinical_documentation_quality/data/nstemi_test5.txt",
what="character",
          sep=",", quote="\"", dec=".", fill=FALSE, comment.char="", allowEscapes=TRUE),
stringsAsFactors=FALSE)
lentest5 <- length(test5[,1])
test5 <- DataframeSource(test5)
test5.corpus <- Corpus(test5)
test5.dtm <- DocumentTermMatrix(test5.corpus, control=ctrl_dtm)
rowTotals <- apply(test5.dtm, 1, sum) # find the sum of words in each Document
test5.dtm <- test5.dtm[rowTotals > 0,]
lda_test5.1 <- LDA(test5.dtm, method="VEM", control=list(alpha=0.1, seed=1231), k=k)
lda_test5.2 <- LDA(test5.dtm, method="VEM", control=list(alpha=0.1, seed=1232), k=k)
lda_perp_test5.1 <- perplx(lda_test5.1)
lda_perp_test5.2 <- perplx(lda_test5.2)
lda_perp_test5 <- c(lda_perp_test5.1, lda_perp_test5.2, + 0.1)
mean(lda_perp_test5) # 27.6
# Welch t-test for difference in perplexities, test vs. train
p <- t.test(x=lda_perp_test5, y=lda_perp_train, alternative="two.sided")$p.value     # p=3.0e-02
p # accept H0
```

FIG. 7C

CONTINUES IN FIG. 7D

CONTINUES FROM FIG. 7C

```
###########################################
# load training data - CLABSI
train <- data.frame(scan(file="c:/0_cerdsm/IP/clinical_documentation_quality/data/clabsi_train.txt",
what="character",
          sep=",", quote="\"", dec=".", fill=FALSE, comment.char="", allowEscapes=TRUE),
stringsAsFactors=FALSE)
lentrain <- length(train[,1])
train <- DataframeSource(train)

# construct corpora from data.frames
train.corpus <- Corpus(train)

# construct DTMs from corpora (preferably, a large plurality of documents that were deemed
# adequately complete and coherent; instead of single document example here)
train.dtm <- DocumentTermMatrix(train.corpus, control=ctrl_dtm)

# remove any rows in pre-processed dtm that have zero entries
rowTotals <- apply(train.dtm , 1, sum) # find the sum of words in each Document
train.dtm <- train.dtm[rowTotals > 0,]

# construct LDA models
lda_train.1 <- LDA(train.dtm, method="VEM", control=list(alpha=0.1, seed=1231), k=k)
lda_train.2 <- LDA(train.dtm, method="VEM", control=list(alpha=0.1, seed=1232), k=k)

# determine perplx of training data
lda_perp_train.1 <- perplx(lda_train.1)
lda_perp_train.2 <- perplx(lda_train.2)
lda_perp_train <- c(lda_perp_train.1, lda_perp_train.2 + 0.1)
mean(lda_perp_train) # 461.5 process test1 data
test1 <- data.frame(scan(file="c:/0_cerdsm/IP/clinical_documentation_quality/data/clabsi_test1.txt",
what="character",
          sep=",", quote="\"", dec=".", fill=FALSE, comment.char="", allowEscapes=TRUE),
stringsAsFactors=FALSE)
lentest1 <- length(test1[,1])
test1 <- DataframeSource(test1)
test1.corpus <- Corpus(test1)
test1.dtm <- DocumentTermMatrix(test1.corpus, control=ctrl_dtm)
rowTotals <- apply(test1.dtm, 1, sum) # find the sum of words in each Document
test1.dtm <- test1.dtm[rowTotals > 0,]
lda_test1.1 <- LDA(test1.dtm, method="VEM", control=list(alpha=0.1, seed=1231), k=k)
lda_test1.2 <- LDA(test1.dtm, method="VEM", control=list(alpha=0.1, seed=1232), k=k)
lda_perp_test1.1 <- perplx(lda_test1.1)
lda_perp_test1.2 <- perplx(lda_test1.2)
lda_perp_test1 <- c(lda_perp_test1.1, lda_perp_test1.2 + 0.1)
mean(lda_perp_test1) # 35.1
# Welch t-test for difference in perplexities, test vs. train
p <- t.test(x=lda_perp_test1, y=lda_perp_train, alternative="two.sided")$p.value    # p=2.3e-05
p # reject H0
```

CONTINUES IN FIG. 7E

FIG. 7D

CONTINUES FROM FIG. 7D

```
test2 <- data.frame(scan(file="c:/0_cerdsm/IP/clinical_documentation_quality/data/clabsi_test2.txt",
what="character",
          sep=",", quote="\"", dec=".", fill=FALSE, comment.char="", allowEscapes=TRUE),
stringsAsFactors=FALSE)
lentest2 <- length(test2[,1])
test2 <- DataframeSource(test2)
test2.corpus <- Corpus(test2)
test2.dtm <- DocumentTermMatrix(test2.corpus, control=ctrl_dtm)
rowTotals <- apply(test2.dtm, 1, sum) # find the sum of words in each Document
test2.dtm <- test2.dtm[rowTotals > 0,]
lda_test2.1 <- LDA(test2.dtm, method="VEM", control=list(alpha=0.1, seed=1231), k=k)
lda_test2.2 <- LDA(test2.dtm, method="VEM", control=list(alpha=0.1, seed=1232), k=k)
lda_perp_test2.1 <- perplx(lda_test2.1)
lda_perp_test2.2 <- perplx(lda_test2.2)
lda_perp_test2 <- c(lda_perp_test2.1, lda_perp_test2.2 + 0.1)
mean(lda_perp_test2) # 140.5
# Welch t-test for difference in perplexities, test vs. train
p <- t.test(x=lda_perp_test2, y=lda_perp_train, alternative="two.sided")$p.value     # p=2.2e-04
p # reject H0 test3 <- data.frame(scan(file="c:/0_cerdsm/IP/clinical_documentation_quality/data/clabsi_test3.txt",
what="character",
          sep=",", quote="\"", dec=".", fill=FALSE, comment.char="", allowEscapes=TRUE),
stringsAsFactors=FALSE)
lentest3 <- length(test3[,1])
test3 <- DataframeSource(test3)
test3.corpus <- Corpus(test3)
test3.dtm <- DocumentTermMatrix(test3.corpus, control=ctrl_dtm)
rowTotals <- apply(test3.dtm, 1, sum) # find the sum of words in each Document
test3.dtm <- test3.dtm[rowTotals > 0,]
lda_test3.1 <- LDA(test3.dtm, method="VEM", control=list(alpha=0.1, seed=1231), k=k)
lda_test3.2 <- LDA(test3.dtm, method="VEM", control=list(alpha=0.1, seed=1232), k=k)
lda_perp_test3.1 <- perplx(lda_test3.1)
lda_perp_test3.2 <- perplx(lda_test3.2)
lda_perp_test3 <- c(lda_perp_test3.1, lda_perp_test3.2 + 0.1)
mean(lda_perp_test3) # 29.6
# Welch t-test for difference in perplexities, test vs. train
p <- t.test(x=lda_perp_test3, y=lda_perp_train, alternative="two.sided")$p.value     # p=2.0e-03
p # accept H0
```

CONTINUES IN FIG. 7F

*FIG. 7E*

CONTINUES FROM FIG. 7D

```
test4 <- data.frame(scan(file="c:/0_cerdsm/IP/clinical_documentation_quality/data/clabsi_test4.txt",
what="character",
           sep=",", quote="\"", dec=".", fill=FALSE, comment.char="", allowEscapes=TRUE),
stringsAsFactors=FALSE)
lentest4 <- length(test4[,1])
test4 <- DataframeSource(test4)
test4.corpus <- Corpus(test4)
test4.dtm <- DocumentTermMatrix(test4.corpus, control=ctrl_dtm)
rowTotals <- apply(test4.dtm, 1, sum) # find the sum of words in each Document
test4.dtm <- test4.dtm[rowTotals > 0,]
lda_test4.1 <- LDA(test4.dtm, method="VEM", control=list(alpha=0.1, seed=1231), k=k)
lda_test4.2 <- LDA(test4.dtm, method="VEM", control=list(alpha=0.1, seed=1232), k=k)
lda_perp_test4.1 <- perplx(lda_test4.1)
lda_perp_test4.2 <- perplx(lda_test4.2)
lda_perp_test4 <- c(lda_perp_test4.1, lda_perp_test4.2 + 0.1)
mean(lda_perp_test4) # 20.3
# Welch t-test for difference in perplexities, test vs. train
p <- t.test(x=lda_perp_test4, y=lda_perp_train, alternative="two.sided")$p.value    # p=1.0e-03
p # reject H0 test5 <- data.frame(scan(file="c:/0_cerdsm/IP/clinical_documentation_quality/data/clabsi_test5.txt",
what="character",
           sep=",", quote="\"", dec=".", fill=FALSE, comment.char="", allowEscapes=TRUE),
stringsAsFactors=FALSE)
lentest5 <- length(test5[,1])
test5 <- DataframeSource(test5)
test5.corpus <- Corpus(test5)
test5.dtm <- DocumentTermMatrix(test5.corpus, control=ctrl_dtm)
rowTotals <- apply(test5.dtm, 1, sum) # find the sum of words in each Document
test5.dtm <- test5.dtm[rowTotals > 0,]
lda_test5.1 <- LDA(test5.dtm, method="VEM", control=list(alpha=0.1, seed=1231), k=k)
lda_test5.2 <- LDA(test5.dtm, method="VEM", control=list(alpha=0.1, seed=1232), k=k)
lda_perp_test5.1 <- perplx(lda_test5.1)
lda_perp_test5.2 <- perplx(lda_test5.2)
lda_perp_test5 <- c(lda_perp_test5.1, lda_perp_test5.2, + 0.1)
mean(lda_perp_test5) # 15.7
# Welch t-test for difference in perplexities, test vs. train
p <- t.test(x=lda_perp_test5, y=lda_perp_train, alternative="two.sided")$p.value    # p=2.7e-04
p # reject H0 alternatively may use Wilcoxon rank-sum test, Tarone-Ware test, or other
```

*FIG. 7F*

DETERMINING ADEQUACY OF DOCUMENTATION USING PERPLEXITY AND PROBABILISTIC COHERENCE

CROSS-REFERENCE TO RELATED APPLICATIONS

This application is a continuation of U.S. application Ser. No. 16/574,735, filed Sep. 18, 2019, and entitled "DETERMINING ADEQUACY OF DOCUMENTATION USING PERPLEXITY AND PROBABILISTIC COHERENCE," which claims to priority to U.S. application Ser. No. 15/854,610, filed Dec. 26, 2017, which claims priority to Provisional Patent Application No. 62/439,151, filed Dec. 26, 2016, and entitled "DETERMINING ADEQUACY OF DOCUMENTATION USING PERPLEXITY AND PROBABILISTIC COHERENCE," the entire contents of which is incorporated herein by reference in its entirety.

BACKGROUND

Ours is an era of services provisioning governed by managerial science and bounded rationality. For example, clinicians and providers of health services are presently compelled by insurers and by regulations to document in writing the services they render to each patient. They must do so in a manner that manifests adequate 'warrant' for believing that clinical care is and was rationally defensible. Implicitly, acting to conclude an episode of care and dismissing the patient is to assert that one's documentation of that episode is sufficient —adequate for safely discharging the person under care; for submitting a claim for payment for the care services that have been rendered and satisfying the reimbursement criteria of the payor; for communicating (to other clinicians who may in the future care for this person) the nature and the indications and contraindications and other salient desiderata that prevailed during the current episode; for conforming to the applicable regulations of government and NGO safety and quality authorities; and for other purposes. That is, a premise of modern healthcare is that it is conducted rationally and transparently, based on sayable, disclosable evidence.

Underpinning the past 40 years' quality-improvement and accountable-care and health reform movements is the high regard in which society holds science and reason and the concepts of evidence, continuous learning, and defensibility. The ad hoc and anecdotal, paternalistic therapeutics of bygone decades is now powerfully discouraged. Even alternative and "integrative" treatments must now show their safety and effectiveness by documented evidence of objective reasons and measured outcomes and rational deliberation.

In health services reimbursed in the U.S. under the Medicare program, inpatient medical services are bundled into a number of Diagnosis Related Groups (DRGs). Hospitals are reimbursed for medical services rendered to patients on per-case flat rate based on the DRG identified for each case. There is a select group of diagnoses that have the potential to impact the DRG used to determine the payment to a hospital. Claims submitted by a hospital for payment may be audited (e.g., RAC Audits). The audits may focus on the diagnoses that impact the DRG payment to determine if the patient data submitted supports the diagnoses. If it is found that a diagnosis is not supported, the DRG payment could potentially be reduced and the hospital would have to pay back the difference. Thus, the evidentiary support for diagnoses or other attributes that are deemed to corroborate and justify the decision to provide a service is subject to review. Such review may either lead to acceptance of the corpus of text and other expository materials as 'adequate' or rejection of the corpus as 'inadequate,' resulting in non-reimbursement or 'claw-back' of payment previously rendered. Besides health services industry, other industries similarly have controls and accountability processes in which the adequacy of supporting text documents is assessed.

In such situations, specific contexts as relate to the decision-making purpose or purposes at hand influence the extent and nature of the evidence that is regarded as necessary, sufficient and pertinent. Contexts that involve life-critical risks or large and/or irreversible financial consequences of decisions reached generally entail larger and more detailed supporting information. In many instances, the expository statements associated with such high-value decision-making contexts also address a large number of aspects or topics that are interrelated and whose interrelationships are characterized in the exposition. By contrast, contexts that involve modest risks or impacts of decisions generally entail small and less detailed supporting information. In most such instances, the expository statements put forward by individuals who are documenting the basis of their reasoning and decision-making address a small number of aspects or topics, and there is less extensive narrative to explain or characterize interrelationships, if any, between the documented topics or aspects.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Technologies are provided for the automatic identification of deficiencies in narrative textual data that may impact decision-making in a decisional context, such as payment for health services rendered to a patient and facilitates collection/correction of patient data to address the deficiencies. In particular, embodiments of these technologies utilize a reference corpus of text to generate a topic model, such as a latent Dirichlet allocation (LDA) topic model or a correlated-topics model (CTM), and determine a corresponding statistical perplexity and probabilistic coherence. The reference corpus may be known or normatively deemed to be epistemically persuasive and adequate with respect to a particular context. The determined topic model then may be applied to a candidate text document (or corpus) whose epistemic properties and adequacy for the decisional purpose is not yet known. Statistical determinations of a degree to which the candidate deviates from the reference normative corpus are determined, in terms of the statistical perplexity and probabilistic coherence of the candidate as compared to the reference. If one or more aspects of epistemic persuasiveness or evidentiary adequacy are abnormal, a message may be reported to user, such as the author or an auditor of the candidate text document, so that the user has the opportunity to amend the candidate document so as to improve its adequacy for the decisional purposes in the context at hand. For instance, when a deficiency in the candidate document is identified, an electronic notification is generated and presented on a user's computing device. In some embodiments, the notification may also facilitate providing access to a user interface that allows the user to enter additional information or clarify information in the data to address the deficiency. Further, some embodiments automatically recognize and alert users regarding inadequate documentation or deficiencies in narrative textual data in near-realtime, enabling the user to immediately correct the documentation.

An aspect described herein is directed to a method for automatically identifying deficiencies in narrative textual data based on a determined statistical perplexity and probabilistic coherence. Some embodiments of the method comprise accessing electronically stored data pertinent to a decision-making process (such as patient data from an electronic medical record for a patient). One or more evidentiary contexts are determined that are associated with the subject matter of the data (such as any of a plurality of diagnoses that impact payment for medical services rendered for the patient are confirmed by a physician in the patient data). A document or a corpus of text comprised of a plurality of text items or documents with the computing device is evaluated. In some embodiments, the evaluation comprises accessing a data storage system with the computing device a candidate document or corpus to be evaluated as to its documentary or evidentiary adequacy by comparison to a retrieved reference corpus of historical text representing documents that have previously been found to be, and classified as, either adequate or inadequate with respect to the evidentiary or decision-making purpose at hand. In some embodiments, the evaluation further comprises accessing, with the computing device, the data storage system to obtain stored stopwords and related linguistic parameters that pertain to said processual or evidentiary purposes. The evaluation may further comprise deriving, with the computing device, a statistical topic model that characterizes the reference corpus and the candidate document or corpus; accessing, with the computing device, the data storage system one model or a plurality of mathematical or statistical topic models that determine(s) the likelihood of evidentiary persuasiveness or acceptability for the decision-making purpose at hand. An electronic employee health record system may be connected to via internet or other computer network so as to incorporate the probabilities into managers' and/or employees' workflow, as a means of decision-support toward timely, prospective, and automatic ascertainment of the adequacy. An electronic message may be generated and transmitted to the clinician computing device associated with the human user, providing a confirmation quality check notification. The transmission of the electronic message over the communication network may cause the application to display the confirmation documentation quality check notification on the user's computing device.

BRIEF DESCRIPTION OF THE DRAWINGS

The present invention is described in detail below with reference to the attached drawing figures, wherein:

FIGS. 4 and 5 depict examples of narrative textual data that may be received in the course of documenting a patient having central-line-associated blood stream infection (CLABSI) and a patient having non-ST-elevated myocardial infarction (NSTEMI), respectively; and FIGS. 6A-6D and 7A-7F illustratively depict examples embodiments of a computer program routine used for determining deficiencies in narrative textual data based on a probabilistic coherence (FIGS. 6A-6D) and perplexity (FIGS. 7A-7F).

DETAILED DESCRIPTION

Figure 1A:
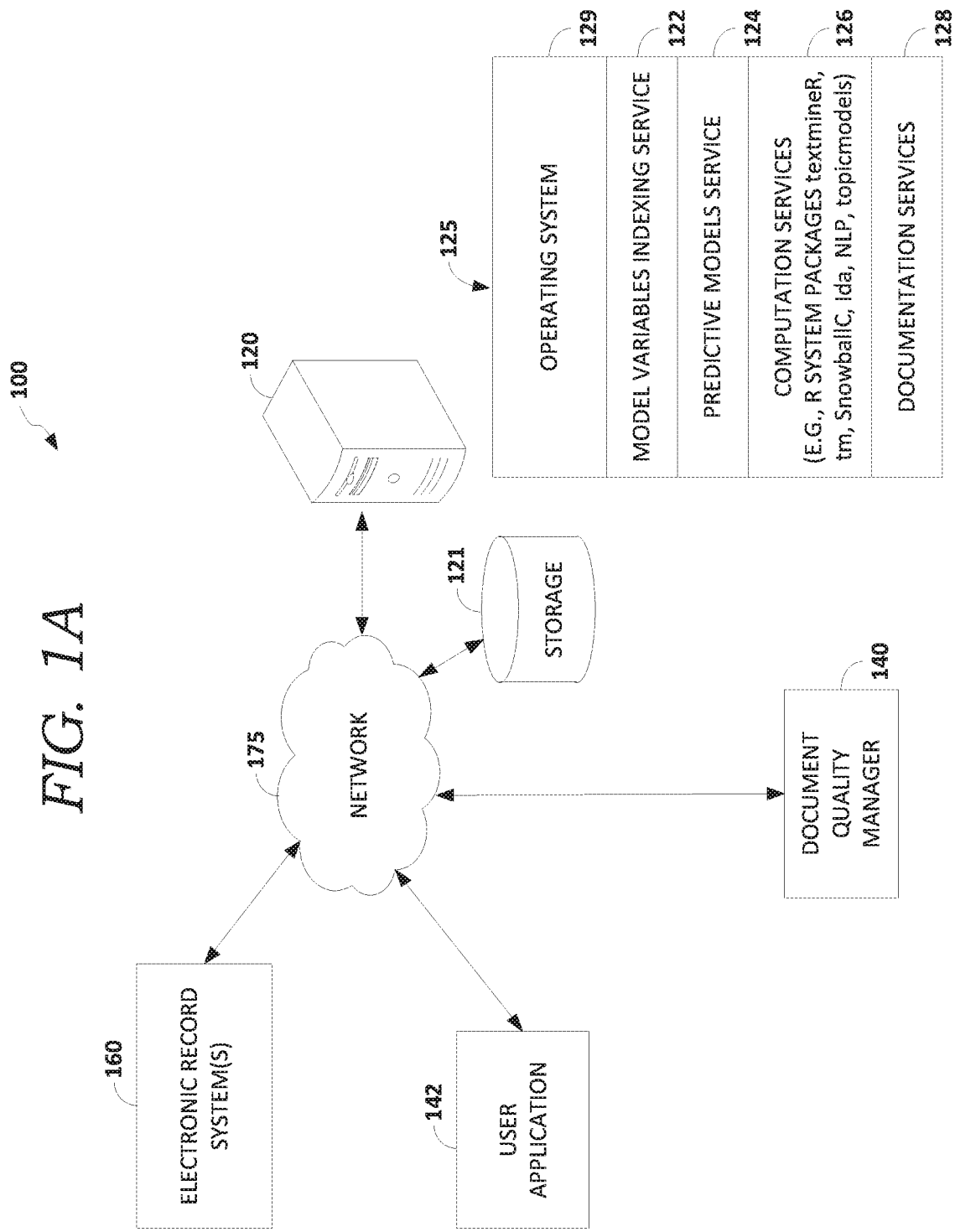
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Aspects of the technology described herein may be utilized for determining deficiencies in narrative textual data including documentation that may impact decision-making in a decisional context. For instance, several example embodiments actually reduced to practice focus on health services and documentation of the services rendered to a patient, as well as the logical basis that established the medical necessity and clinical appropriateness of the decisions leading to the provisioning of those services, which is supported from documentation, which may also have a bearing on payment for the health services rendered. In particular, embodiments of the technologies described herein utilize a reference corpus of text to generate one or more topic models, such as a latent Dirichlet allocation (LDA) topic model or a correlated-topics model (CTM), and then determine a corresponding statistical perplexity and probabilistic coherence. The reference corpus may be known or normatively deemed to be epistemically persuasive and adequate with respect to a particular context. The determined topic model then may be applied to a candidate text document (or corpus) having a similar context and whose epistemic properties and adequacy for the decisional purpose is not yet known, and a comparison performed to determine statistical differences. Based on a degree of difference(s), the candidate document is determined include adequate or inadequate documentation. In some embodiments, the candidate document author or an auditor (such as a clinician or document quality manager is provided an electronic notification of document inadequacy and may further be presented with a user interface and the candidate document so that the documentation can be corrected to me made adequate.

As described above, in the current era, clinicians and providers of health services are presently compelled by insurers and by regulations to document the services they render to each patient. They must do so in a manner that manifests adequate 'warrant' for believing that clinical care is and was rationally defensible. Similarly, the practice of law and other disciplines may be required to establish normative and statistical evidentiary practices that are suited to the contexts and to the decision-making idioms that prevail within the scope of their practice. Thus the candidate documents described herein may include narrative textual data that may impact decision making in a particular decisional context. For example, payment of health services rendered to a patient. Experts sometimes may be used to establish these norms, while in other instances a large and representative corpus of de facto historical documents may be used to determine normative or common practice.

The warrant given in the documentation produced in medicine, law, or other disciplines should be adequate, among other things, in terms of its 'coherence:' that is, it should meet de facto scientific, social, legal, and/or regulatory norms. In health services, the context of what disease(s), if any, the patient had at the time that the services were rendered, the age and gender of the patient as may relate to ancillary risks and preventive care that would be germane, the role and specialty of the clinician(s) who rendered the service(s), the duration of the care episode, and the venue type where the episode occurred must be documented, among other factors. Such norms are, whether stated outright or not, statistical norms. Embodiments described herein provide systems and methods for determining, quantitatively, the epistemic persuasiveness and evidentiary adequacy of a corpus of texts comprising the documentation associated with a service episode, as compared to one or more normative reference corpora whose evidentiary adequacy is known, in the same context and with respect to the same decisional purposes.

Accordingly, as will be further described herein, one embodiment comprises a method for automatically identifying deficiencies in narrative textual data based on a determined statistical perplexity and probabilistic coherence. For a particular case to be documented (such as, a patient being treated for a condition or undergoing a procedure), a candidate text document (or text corpus) associated with the case is identified. The text documents may be created by (or their creation facilitated by) a caregiver, clinician, or the patient, for example; and the information contained in the text documents may come from speech (i.e. spoken narrative that is converted to speech via a computer process), typed-entry, or provided from a clinical computer program that generates automatically logs of certain activity. In some embodiments, a plurality of candidate text documents is used instead of a single candidate, and further, the plurality of documents may be evaluated together, as though they were a single document. The candidate text document may be pre-processed using a natural language processing (NLP) computing system or program to identify context-relevant terms contained in the document; for instance, in one embodiment, Cerner's nCode NLP system is utilized. In some embodiments, the identified context-relevant terms are determined by clinical codes, such as ICD-9 codes.

A context to which the documentation and evidentiary adequacy review pertains is determined. For example, many patient treatments or procedures or related activities (such as claims or payment) have specific policies or laws regarding documentation. The context may be provided by a user-clinician; may be determined automatically based on information contained in the candidate document (e.g., a patient, a particular treatment, or procedure indicated in the candidate document); or may be determined by other contextual information associated with the candidate document. By way of example, the other contextual information might include information derived from a patient's electronic health record (EHR), caregiver's context (e.g., the caregiver only administers certain procedures, such as radiology procedures from which a context is pre-determined, a schedule of the caregiver or patient when the candidate document was created, etc. In some instances, a clinician may be prompted to confirm a particular context to which the documentation and evidentiary adequacy review pertains is determined.

The text in the candidate text document may be pre-processed. For example, word stemming may be applied or the removal of stop words, punctuation, short words, etc. In some embodiments, the R-packages R NLP, tm, and SnowballC may be utilized in step 230. One or more topic models is then generated for the candidate document, such as a latent Dirichlet allocation (LDA) topic model or a correlated-topics model (CTM). In some embodiments, document-term matrices (DTMs) are also determined, and in some instances, the DTMs may be pre-processed to remove any empty rows.

Based on the context to which the documentation and evidentiary adequacy review pertains, one or more topic model(s) and DTMs, which are generated from a reference text corpus having a similar context, are identified and accessed. The reference corpus may comprise one or more documents that are known or normatively deemed to be epistemically persuasive and adequate with respect to the particular context. In some embodiments, where the reference corpus topic model(s) and DTMs are not generated yet, step 250 comprises identifying a reference corpus having a similar context to the context determined in step 220, and then generating the topic model(s) and DTMs for the reference corpus. In particular, in some embodiments steps 240 may be applied to the reference corpus; and further, in some embodiments, step 230 (preprocessing) also may be applied to the reference corpus prior to generating the topic model(s) and DTMs.

A probabilistic coherence is determined for each topic, and a statistical perplexity of the candidate document and reference corpus is also determined. An example of determining probabilistic coherence is provided in the example computer program routine of FIGS. 6A-6D, and an example of determining statistical perplexity is provided in the example computer program routine of FIGS. 7A-7F. A comparison is then performed to determine statistical differences between the candidate document and reference corpus. In an embodiment, step 270 comprises utilizing string matching to establish which topics associated with topic model(s) of the candidate document correspond to which topics associated with the topic model(s) of the reference corpus. A Kendall tau test, paired Wilcoxon sign-rank text, or other paired test is performed to determine statistical significance of difference candidate and reference probabilistic coherence vectors. Then a Welch t-test, Wilcoxon rank-sum, or other suitable test is performed to determine statistical significance of difference between candidate document and reference corpus perplexity.

Based on these statistical difference(s), the documentation of the candidate document is determined either to be adequate or inadequate. In some embodiments, statistical significance of difference is evaluated against a threshold, and if the threshold is satisfied, then the difference is considered significant enough to warrant notification of the candidate document as being inadequate. Otherwise, the documentation of the candidate document may be considered adequate. The threshold may be predetermined and/or may be determined based on the context of step 220. If the documentation is adequate, then the it may be noted that the document has passed review for adequacy. In some embodiments, the document may be updated to include an indicator (for instance a marking or content added to the document (such as a notification added as a footnote) or metadata associated with the candidate document) indicating that the candidate document includes adequate documentation. However, if the documentation is determined to be inadequate, then a notification may be issued indicating that the documentation is inadequate. For example, an electronic signal may be generated indicating that the documentation is inadequate. In some embodiments, the candidate document may be flagged or pulled for further review or for editing in order for the documentation to be adequate. The notification may be provided to a document quality manager, via manager application 140 or may be provided to the creator or author of the candidate document so that that person can edit or amend the candidate document in order to make the documentation sufficiently adequate. In some embodiments the editing or amending may be facilitated by user application 142.

In this way, embodiments described herein provide improvements to existing technologies related to document quality ascertainment. In particular, embodiments overcome significant limitations of the conventional technologies for document quality ascertainment including: (a) that conventional approaches are overly simplistic, such that the algorithms utilized by these conventional technologies give rise to inaccuracies, including excessive false-negative error rates, which result in laxity or failures to detect evidentiary inadequacy or fitness-for-purpose and failures to amend or correct the deficiencies in a timely manner, and including excessive false-positive error rates, resulting in needless review and, sometimes, erroneous amending of documentation that does not merit such review and amending; (b) that they fail to take into account a variety of detailed attributes of the contexts in which the documentary evidence is prepared and reviewed; (c) that they entail cumbersome or expensive procedures, including manual human curation of tables that define the relationships among terms that constitute evidence supporting or discorroborating particular propositions or statuses (such as clinical evidence that supports the ascription of a diagnosis, or diagnoses that support the performance of a diagnostic or therapeutic procedure or prescribing of a medication); (d) they are not amenable to continuous monitoring and automatic processing. Notably, these problems and the other failures of previously attempted solutions discussed herein cannot be overcome by simply using a computer. For example, conventional technological systems developed to address these, and other limitations, have failed to remove human bias and subjectivity from manual human curation of tables that define the relationships among terms, manual review and approval of documents or corpuses. This is because the problems with the conventional technology require new and improved techniques that specifically overcome these drawbacks. Hence, the embodiments discussed herein overcome these disadvantages by implementing new and improved techniques and features that are not know in conventional industry practice, thereby providing enhanced decision support systems that are capable producing reliable and accurate determinations that have not been previously achieved.

By way of background, it is noteworthy that many terms can be used to evaluate beliefs, belief-forming processes, and other similar mental states and processes of reasoning that result in a determination of evidentiary adequacy. Such mental states and processes can be called "right" or "wrong", "correct" or "incorrect", "reasonable" or "unreasonable", "justified" or "unjustified", and so on. Many philosophers evaluate mental states or processes of reasoning by saying that they are mental states that the decision-maker in question is "entitled" to have, or processes of reasoning that the decision-maker is "entitled" to perform. A central part of epistemology is concerned with investigating the conditions under which decision-makers are in this sense "entitled" to various beliefs and processes of belief-formation or belief-revision.

Other epistemologists favor the word 'rationality'. This term is particularly popular among linguistic scientists and formal epistemologists—such as those in the Bayesian tradition, which emphasizes mathematical conceptions of plausibility or probability. According to this alternative tradition, the central questions of epistemology concern the conditions under which our beliefs, and the processes by which we form and revise our beliefs, count as "rational." The terms 'rationality' and 'entitlement' arise from different epistemological traditions, but they express the same range of concepts. Both terms, when they are used by epistemologists in these ways, express broadly normative concepts. The term 'entitlement' expresses a normative principles involving systems of institutional rules. For example, if you are "entitled," under the rules of the enterprise that you work for, to go on vacation leave for a certain period of time each year, then according to those rules, it is permissible for you to go on vacation for such a period; and if you communicate your intention to go on leave, then the enterprise will normally be obliged to allow you to take that period of leave. Similarly, the term 'rational' can also be used to express a normative concept—specifically, a concept that refers to the proper use of one's faculties of thinking and reasoning. For example, to say that you "rationally believe" a certain proposition p is to say that in believing p, you are using these faculties properly in the relevant sense; and to say that "it is rational" for you to believe a certain proposition q is to say that there is a possible process of reasoning, consisting of the proper use of these faculties, that leads from your current state of mind to your believing q.

Among epistemologists who use the term 'entitlement' it is widely supposed that "entitlement" differs in an important way from "justification." In fact, different philosophers have proposed several different contrasts between justification and entitlement. For example, Wright says that entitlement is "a kind of rational warrant" for accepting a proposition that is not to be identified with "having evidence for its truth." For both Avnur and Wright, then, entitlement differs from other kinds of warrant in that entitlement does not require "evidence".

An overwhelming majority of formal epistemologists would likely agree that there are many cases where it is rational for a decision-maker to have a certain level of confidence in a proposition p, and what makes it the case that this is rational is not any "evidence" that the agent possesses for or against this proposition p. According to proponents of Bayesian approaches, the rational decision-maker need not have the concepts of probabilistic coherence, or of a warrant, or of a "reason," or anything of that sort. She need not have the concept of evidence or even the concept of belief; she need not even have the concept of experience or perception, or the concept of a belief's being incoherent. According to the subjective Bayesians, all that is required is that the decision-maker's beliefs must actually be probabilistically coherent, and they must evolve in response to evidence by means of conditionalization. Objective Bayesians would impose further conditions, but none of the conditions that have been proposed require that the decision-maker must possess any of these concepts. Here too, then, the notions expressed by the term 'entitlement' seem to coincide with those that are expressed by 'rationality'.

However, even if it is intuitively plausible that mental states that are dominated in this way are always irrational, it is not clear that this sort of dominance is what explains why they are irrational. The trouble is simply that this sort of explanation seems likely not to be sufficiently general. It is plausible that for some requirements of rationality, there are not only worlds where satisfying the requirement will result in your doing better in terms of correctness, but also some worlds where satisfying the requirement will result in your doing worse. For example, suppose that rationality requires you to be non-skeptical: that is, it requires you to take your sensory experience at face value—to respond to your having an experience as of a proposition p's being the case (at least so long as you consider the question of whether p is the case, and no undermining or defeating evidence is present) by having a high level of confidence in p. Presumably, however, your mental states are not telling you that the patient could not possibly have a stroke so the space of worlds will include some worlds where this patient does indeed have a stroke and in those worlds, satisfying this requirement will lead you to do less well with respect to your beliefs' degree of incorrectness than some ways of violating the requirement. So not every way of violating this requirement is dominated by some way of satisfying this requirement; this requirement cannot be explained by appealing to dominance in this way. Still, it may be that the worlds in which satisfying this requirement leads you to do better, in terms of your beliefs' degree of incorrectness, than every way of violating the requirement take up a larger proportion of this space of worlds than the worlds where violating the requirement leads you to do better in this way. This may be what explains why rationality requires reviewers to take clinicians' observations at face value.

In general, to determine the degree of rationality of each mental state that the decision-maker could have, we could consider each of these mental states as partitioning this space of worlds into sub-regions or domains, such that for every one of these domains, the mental state in question have the same degree of incorrectness at every world in that domain. Then we could weight this degree of incorrectness by the proportion of the whole space of worlds that is taken up by the worlds in that domain; the average of these weighted degrees of correctness will be this mental state's weighted average of incorrectness across this whole space of worlds. In general, then, we propose that one mental state is more rational than an alternative just in case the first state has better weighted average degree of incorrectness, across this whole space of worlds, than the second alternative state.

This conception of the relationship between correctness and rationality evidently requires this space of worlds to be a measurable space, in the sense that there are definite ratios between the different proportions of this space. So, for example, it could be that the worlds where one proposition p is true take up twice as large a proportion of this space as the worlds where another proposition q is true. In fact, the relevant measure on this space is in effect a probability distribution over these worlds. In effect, the connection between rationality and correctness that the present invention teaches is, amongst other things: rationality minimizes expected incorrectness—where the relevant "expectation" is defined in terms of this probability measure on this space of worlds.

As such, requirements of evidentiary persuasiveness and rationality—including both the requirements of rational belief and those of rational choice—may be explained in the same way. First, for each kind of mental state there is some external "aim"—a standard of adequacy or correctness that provides a way of measuring the degree of incorrectness that every mental state of that kind has at every possible world. Secondly, for every decision-maker at every time, there is a measurable space of worlds of the kind—where the measure on this space of worlds is in effect a probability measure. Finally, these two elements together determine an expected degree of incorrectness for every mental state; and according to my proposal, a mental state's degree of irrationality can be identified with its expected degree of incorrectness.

Some embodiments described herein contemplate that evidentiary persuasiveness or rationality optimizes—that is, minimizes—expected incorrectness, where "expectation" is defined in terms of this probability distribution on the relevant space of epistemically possible worlds. According to this proposal, a notion of maximizing the expectation of some value is an aspect of rationality in a social and regulatory setting, such as provisioning and paying for health services. In some contexts, "checklist" instruments are used to encourage or enforce conformity to normative standards for documentation adequacy. Both errors of commission and errors of omission are known to occur. This sort of approach may be conceived as reducing all of rationality to practical rationality or decision theory, thereby reconceiving epistemology as a kind of "epistemic utility theory."

In some instances, this approach may be 'supervised' (curated under the leadership of people who are broadly acknowledged to be experts in the field of the health services whose rational basis is in question) or it may be automatically determined and thus unsupervised, such as for instances where the corpus of textual materials and number of accumulated exemplar cases is large.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of this disclosure, which in some embodiments may include collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Environment 100 includes electronic record system(s) (ERS) 160, which may be part of one or more electronic health record (EHR) systems, communicatively coupled to network 175, which is communicatively coupled to computer system 120. In some embodiments, components of environment 100 that are shown as distinct components may be embodied as part of or within other components of environment 100. For example, ERS 160 may comprise one or a plurality of record/logging systems such as sensor/monitor logging systems, hospital EHR systems, health information exchange EHR systems, clinical genetics/genomics systems, ambulatory clinic EHR systems, psychiatry/neurology EHR systems, insurance, collections or claims records systems; and may be implemented in computer system 120. In an embodiment, ERS 160 includes historical data for patient addition treatment, relapse information, other health services, claims data, apportionment data, and/or related health services financial data.

In some embodiments, sequence itemset mining is performed using data about a population of patients derived from patient EHR information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of ERS 160 may comprise one or more data stores of health records, which may be stored on storage 121, and may further include one or more computers or servers that facilitate the storing and retrieval of the health records. In some embodiments, ERS 160 may be implemented as a cloud-based platform or may be distributed across multiple physical locations. ERS 160 may further include one or more record systems, which store real-time or near real-time patient (or user) information, such as wearable, bedside, or in-home patient monitors or sensors, for example. Although FIG. 1A depicts an exemplary ERS 160, it is contemplated that an embodiment relies on document quality manager 140 and/or user application 142 for accessing, storing and/or retrieving patient record information.

Example operating environment 100 further includes a user application 142 communicatively coupled through network 175 to ERS 160. Although environment 100 depicts an indirect communicative coupling between application 142 and ERS 160 through network 175, it is contemplated that an embodiment of application 142 is communicatively coupled to ERS 160 directly. An embodiment of application 142 comprises a software application or set of applications residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the disclosure, which may be used by a caregiver or patient for receiving information documenting an aspect of activity, such as a text narrative describing a procedure administered to a patient. The information may be received as speech (and converted into a text corpus via an automatic speech recognition (ASR) program or speech-to-text software), received as typed, keyed, or otherwise entered in (e.g. selected from a graphical user interface), or may be received from another computer application or program that automatically generates summaries of patient-related activity conducted via the other computer application or program. For example, a particular patient monitor might record an instance of each time a patient leaves her bed or a smart pill box might record a note each time a particular patient opens (or does not open, when she should open) a compartment to receive her medication.

Some embodiments of user application 142 include a graphical user interface enabling a caregiver (or patient) to enter narrative information for documentation, and may further include one or more graphical user interface elements for presenting or receiving information about a context associated with a particular activity being documented (such as a particular procedure administered to a patient); and one or more graphical user interface elements for presenting a notification that a particular candidate document includes inadequate or adequate documentation. For instance, in one embodiment, a colored icon or highlighted window boundary may indicate adequacy or inadequacy, such as a red "X" for inadequacy or green checkmark for adequacy. Further still, some embodiments of application 142 include a user interface for correcting or amending candidate documents that are determined to be inadequate. Application 142 also may facilitate receiving and logging session or program event information about a particular user, candidate document, or reference corpus, and/or processing, interpreting, accessing, storing, retrieving, and communicating information associated with session logged records or other healthcare related records of the target user or reference corpus.

Example operating environment 100 also includes a document quality manager 140 communicatively coupled through network 175 to ERS 160 and user application 142. In one embodiment of manager 140 comprises a user interface and/or application that may be used to facilitate access by a document quality manager-user (including a clinician/caregiver such as a medical or psychiatric caregiver, an auditor, supervisor, employer, parole officer, etc.) to a particular target patient/user's health records (including information logged in ERS 160, such as candidate document(s)), reference corpora, topic models, DTMs, statistical comparisons, and other aspects of determining adequacy of a candidate document documentation as described herein.

Embodiments of document quality manager 140 that take the form of a user interface and application may be embodied as a software application operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, manager 140 includes a Web-based application (which may take the form of an applet or app) or set of applications usable to manage user services provided by an embodiment of the disclosure.

In some embodiments, manager 140 facilitates accessing and receiving information from a health record, or health care provider about a specific patient, set of patients, or provider clinicians, according to the embodiments presented herein. Embodiments of manager 140 also may facilitate accessing and receiving information from a user or health care provider about a specific patient or population of patients including patient history; health care resource data; variables measurements, timeseries, reference corpora; and predictions (including plotting or displaying the determined outcome and/or issuing an alert) described herein; or other health-related information, and facilitates the display of results, recommendations, or orders, for example. In an embodiment, manager 140 also facilitates receiving orders for the patient/target user from the clinician/caregiver/manager, based on the results of monitoring, predictions, and/or statistical differences described herein. Manager 140 may also be used for providing diagnostic services or evaluation of the performance of various embodiments.

Example operating environment 100 further includes computer system 120, which may take the form of a server, which is communicatively coupled through network 175 to ERS 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on application 142. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running manager 140 and application 142. In some embodiments, application 142 and/or manager 140 operate in conjunction with software stack 125.

In embodiments, model variables indexing (or mapping) service 122 facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126. Predictive models service 124 comprises the topic models described herein, which may include one or more topic models generated from a reference corpus, and which may be developed and implemented according to the method described in connection to FIG. 2.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project. org) or similar services, and R-system modules or packages including, in an embodiment, textmineR and tm packagez, which may be utilized for text mining and topic modeling; package SnowballC, which may be utilized for pre-processing text including stemming to facilitate collapsing words to a common root to aid comparison of vocabulary (stemming); package NLP, which may be utilized for natural language processing, and which may include an interface for openNLP; lda or Collapsed Gibbs Sampling Methods for Topic Models, which may be utilized for implementing latent Dirichlet allocation (LDA) and related models; and topicmodels, which may be utilized for fitting topic models. In some embodiments, computational services 126 may include one or more open source libraries, such as text2vec from GitHub (available at: https://github.com/dselivanov/text2vec). Computational services 126 also may include natural language processing services (not shown) such as Discern nCode™ developed by Cerner Corporation, or similar services. In an embodiment, computation services 126 include the services or routines, which may be embodied as one or more software agents or routines such as the example embodiments of computer program routines illustratively provided in FIGS. 6A-6D and 7A-7F. In some embodiments, computation services 126 use ERS 160. Some embodiments of computation services 126 may use documentation services 128. Documentation services 128 include services for facilitating activity documentation, auditing, and correction, by a clinician-user or document quality manager, which may be facilitated using application 142 and/or manager 140.

Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with ERS 160. Further, although depicted as a single storage data store, data store 121 may comprise one or more data stores, or may be in the cloud.

Figure 1B:
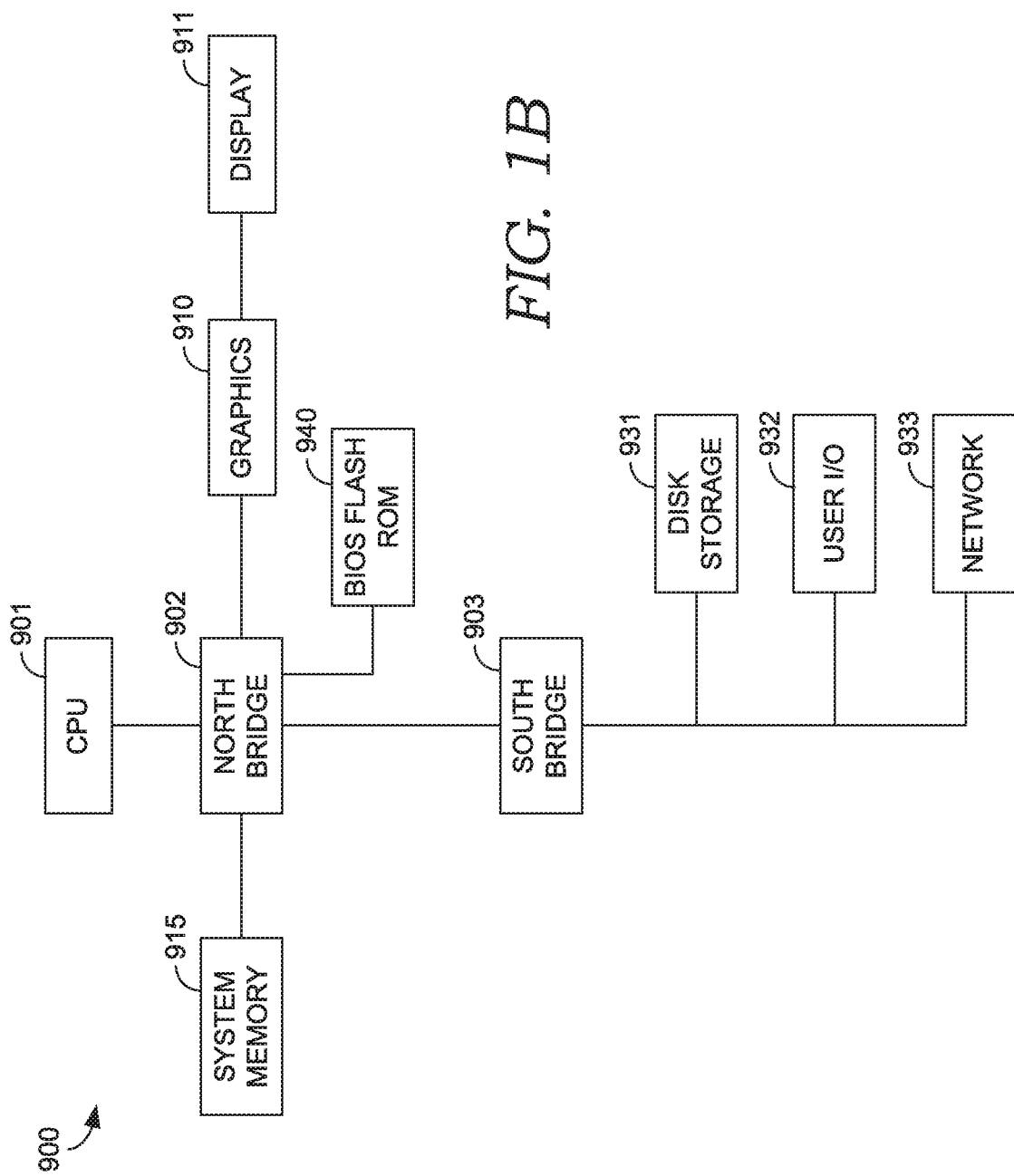

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
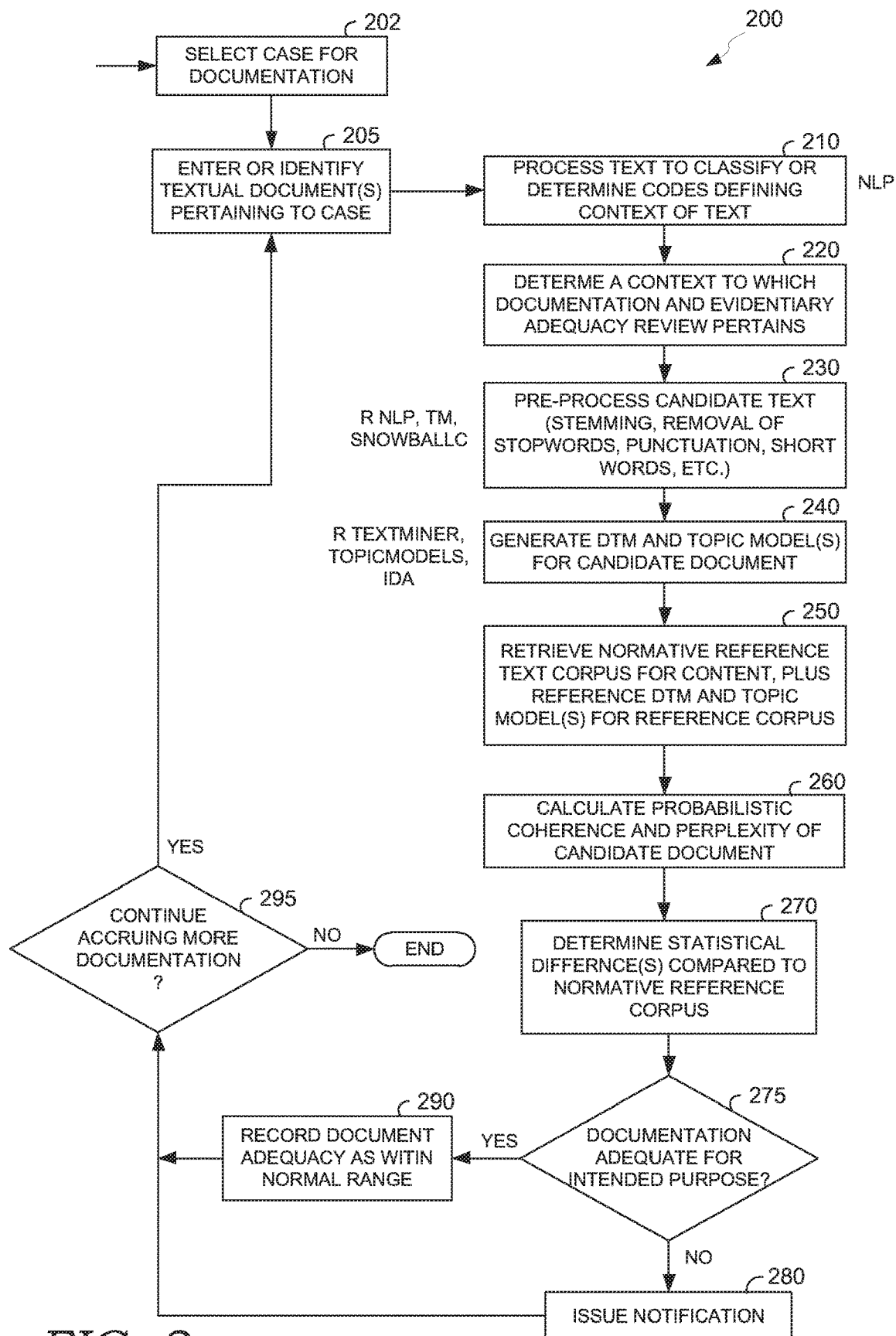
FIG. 2 depicts a flow diagram of a method for automatically identifying deficiencies in narrative textual data based on a determined statistical perplexity and probabilistic coherence, in accordance with an embodiment of the disclosure.

Turning now to FIG. 2, a method 200 is provided for automatically identifying deficiencies in narrative textual data based on a determined statistical perplexity and probabilistic coherence. Some embodiments of the steps of method 200 may be carried out using one or more computer program routines, such as the routine illustratively provided in FIGS. 6A-6D and 7A-7F. Additionally, some embodiments are described which may be incorporated into a computer-performed decision support tool (which may be part of a document quality management system or auditing system).

With reference to FIG. 2 and method 200 generally, an objective of embodiments described in connection to FIG. 2 includes determining certain statistical properties of corpora of reference texts whose epistemic or evidentiary persuasiveness and adequacy is previously established (which, as described above, may be determined automatically or via a panel of experts, or, in the case of health services-related documents, by adjudication by insurers and approval for payment for the services whose delivery and whose clinical indications and logical basis for delivery is documented by the texts) and, using such reference corpora and the statistical properties, to further determine the norms-based adequacy of other candidate documents whose epistemic persuasiveness is at first unknown.

Textual perplexity is mathematically defined as the reciprocal geometric mean of the term or token likelihood in the topic model, as follows:

$$\text{perplexity} = \exp\left\{-\frac{\sum \ln(p(w_d \mid a_d))}{\sum N_d}\right\} \quad (1)$$

Probabilistic coherence has several alternative definitions in prior art research literature which differ in small but important ways. In one embodiment, coherence is defined as follows:

$$\text{coherence} = \frac{P(A_1 \; A_2 \; \ldots \; A_n)}{P(A_1) \times P(A_2) \times \ldots \times P(A_n)} \quad (2)$$

wherein the denominator is the probability that the conjunction of terms would have if the constituents were statistically independent of each other and the numerator is the term co-occurrence probability that is manifested in the actual document or corpus. As such, coherence represents cross-correlations between pairs of terms and among higher-order combinations of terms. The coherence thereby measures the degree to which the co-occurrence of terms exceeds the expected independent co-occurrence by chance, were the terms not semantically correlated and frequently deployed for a communicatively meaningful, epistemologically persuasive, and [coherently] expressive purpose.

Neither probabilistic coherence nor statistical perplexity have been previously applied to determine evidentiary adequacy of documents or corpora comprised of textual documents nor to ascertaining documentation quality or evidentiary adequacy. The concept of coherence is often associated with philosophy of science and epistemology. A theory that is coherent is by many believed to be a better theory than one that is not, all else being equal. But despite the intuitive interpretation of coherence as 'hanging together well' being virtually uncontested, a formal explication has not been forthcoming. Instead, a common complaint by those who refuse to attach any methodological or epistemological value to coherence is that the notion is vague.

In one different sense, coherence may be considered as a confidence boosting property. In that regard, coherence cannot be equated with logical consistency: clearly a system can be intuitively very incoherent even if it is logically consistent. Arguably, this is what happens if, for instance, two beliefs make each other extremely unlikely without logically contradicting each other. A similar argument shows that coherence must be less strict than logical entailment: two beliefs (or propositions) can be very coherent without one of them entailing the other.

Almost all prior efforts regarding probabilistic measures of coherence place emphasis on the notion of coherence as (a) mutual probabilistic support or (b) relative 'overlap' in terms of entailment of a given concept by one or more others, or in terms of dependence of a given concept upon one or more others. Some efforts have described coherence explicitly as a measure of mutual support, and other efforts give mutual support a central place in their theory of coherence, as well. Still other approaches propose other coherence measure in terms of entailment. Some embodiments described herein, and in particular in connection to FIG. 2, contemplate the use of at least one such coherence measure but may optionally employ a plurality of said measures, using a mean or a majority-vote or other methods of combining the results from the multiple measures.

Embodiments described herein contemplate that, in any given context, epistemically persuasive documents and corpora that are deemed to be fit-for-purpose and adequate in terms of evidence they contain do exhibit a range of probabilistic coherence values and a range of perplexity values that are associated with status of epistemic persuasiveness and documentary adequacy. A collection of such documents or corpora might be said to be euperplex and eucoherent.

Documents that are either deficient in perplexity or excessive in their perplexity compared to such a norm might be said to be hypoperplex or hyperperplex, respectively. In the former class are terse or truncated documents that fail to include terms that are associated with the range of topics that are ordinarily addressed in documents that are representative of a particular context and purpose. In the latter class are documents that are a bricolage of disparate, prolix, or overly-synoptic constituent segments that omit many transition or relational expressions that the normative set of documents ordinarily contain.

Documents that are either deficient in coherence or excessive in their probabilistic coherence compared to such a normative collection might be said to be hypocoherent or hypercoherent, respectively. In the former class are abnormally long or disorderly texts or ones that use vocabulary that is abnormally profuse compared to other documents or corpora in the context. The purpose- and context-related expressions are diluted in a sea of terms that are disparate from ones that commonly occur in the normative corpora. In the later class are abbreviated or overly conclusive or over-simplified expository texts that omit use of terms commonly associated with epistemically persuasive, adequate documents.

Accordingly, at a high level, an embodiment of method 200 generates a latent Dirichlet allocation (LDA) topic model or a correlated topics model (CTM) from the extant document text, and the statistical perplexity and probabilistic coherence are determined—firstly, in a reference corpus of text that is known or normatively deemed to be epistemically persuasive and adequate with respect to said context and, secondly, in a candidate text document or corpus whose epistemic properties and adequacy for the decisional purpose is not yet known. Statistical determinations of the degree to which the candidate deviates from the reference normative corpus are made in terms of the statistical perplexity and probabilistic coherence of the candidate as compared to the reference. If one or more aspects of epistemic persuasiveness or evidentiary adequacy are abnormal, a message is reported to the user so that the user has the opportunity to amend the candidate document so as to improve its adequacy for the decisional purposes in the context at hand.

When a deficiency in candidate document adequacy is identified, an electronic notification is generated and delivered over a communication network to a human user's computing device. The notification also may provide the user access to a user interface that allows the user to enter additional information or to correct or clarify information in the candidate documentation corpus to address the deficiency.

In particular, method 200 begins at step 202, wherein a case for documentation is determined. For example, the case may comprise administration of a particular procedure or operation, a patient being treated for a condition or undergoing a procedure, or a particular activity or series of actives for which documentation is required or desired. At step 205, a candidate textual document or text corpus pertaining to the case is entered or is identified. The text documents may be created and entered by (or their creation and/or entering facilitated by) a caregiver, clinician, or the patient, for example; and the information contained in the text documents may come from speech (i.e. spoken narrative that is converted to speech via a computer process), typed-entry, or provided from a clinical computer program that generates automatically logs of certain activity, and may be unstructured or structured data. In some embodiments, a plurality of candidate text documents is identified (or created and/or entered) instead of a single candidate document, and further, the plurality of candidate documents may be evaluated together, as though they were a single document. In an embodiment, the size of a candidate document or corpus is less than 100 words, equal to 100 words, or greater than 100 words exclusive of stopwords. In an embodiment, the size of a candidate document or corpus is less than 500 words, equal to 500 words, or greater than 500 words. In an embodiment, the size of a candidate document or corpus is less than 30,000 words, equal to 30,000 words, or greater than 30,000 words.

At step 210, the candidate text document is processed to classify the text and identify context-relevant terms contained in the candidate document. Embodiments of step 210 may use a natural language processing (NLP) computing system or other computation services 126 (of FIG. 1A); for instance, in one embodiment, Cerner's nCode NLP system is utilized. In one embodiment, Apache OpenNLP may be utilized, and in some embodiments, the identified context-relevant terms are determined a clinical concept codes, such as ICD-9 codes.

At step 220 a context to which the documentation and evidentiary adequacy review pertains is determined. For example, many patient treatments or procedures or related activities (such as claims or payment) have specific policies or laws regarding documentation. The context may be provided by a user-clinician; may be determined automatically based on information contained in the candidate document (e.g., a patient, a particular treatment, or procedure indicated in the candidate document); or may be determined by other contextual information associated with the candidate document. By way of example, the other contextual information might include information derived from a patient's electronic health record (EHR), caregiver's context (e.g., the caregiver only administers certain procedures, such as radiology procedures from which a context is pre-determined), a schedule of the caregiver or patient when the candidate document was created, etc. Further, evidentiary contexts may be determined based on the subject matter of the data contained in the candidate document (such as a diagnoses that impact payment for medical services rendered for the patient are confirmed by a physician in the patient data). In some instances, a clinician may be prompted to confirm a particular context to which the documentation and evidentiary adequacy review pertains is determined.

At step 230, the text in the candidate document may be pre-processed in some embodiments. For example, word stemming may be applied or the removal of stop words, punctuation, short words, etc. A stop word may be a part of speech that are inconsequential to the evidentiary strength of the documentation. For example, articles may be a stop word in some contexts. Further, stemmed words having length smaller than a predefined threshold may be removed. In some embodiments, one or more computation services 126, described in FIG. 1A, such as the R-packages R NLP, tm, and SnowballC may be utilized in step 230.

At step 240, one or more topic models is then generated for the candidate document, such as a latent Dirichlet allocation (LDA) topic model or a correlated-topics model (CTM). The alpha parameter for topic model generation is a value between 0.05 and 0.90, between 0.10 and 0.25, or between 0.01 and 0.99. The number of topics k may be between 2 and 40, between 4 and 20, between 5 and 15, or between7 and 12. The number of words M to be used for matching topics for the purpose of probabilistic coherence comparison is preferably between 4 and 20, more preferably between 5 and 12. In some embodiments, a plurality of stemmed words that are associated with each topic generated in the topic model for the reference corpus are utilized for matching against a plurality of words associated with each topic generated in the topic model for the candidate.

In some embodiments, document-term matrices (DTMs) are also determined, and in some instances, the DTMs may be pre-processed to remove any empty rows. In some embodiments of step 240, computation services 126 are utilized, such as the R-packages testmineR or TopicModels, or other computational services 126 described in connection to FIG. 1A. An example embodiment of generating DTM and topic models of step 240 is provided in the computer program routine illustratively shown in FIGS. 7A-7F. Further, in some embodiments, sparse-array methods are utilized to compactly represent said DTM and related arrays in computer memory and storage media At step 250, based on the context to which the documentation and evidentiary adequacy review pertains determined in step 220, a reference corpus having a similar corpus is identified, and one or more topic model(s) and DTMs are identified and accessed. The reference corpus may comprise one or more documents that are known or normatively deemed to be epistemically persuasive and adequate with respect to the particular context, as described herein. For example, in an embodiment, the reference corpus is less than 300 documents, equal to 300 documents, or greater than 300 documents. Further, the reference corpus may comprise a plurality of words. For example, in some embodiments the reference corpus is less than 30,000 words, equal to 30,000 words, or greater than 30,000 words. Further, the reference corpus may comprise approximately comparable numbers of documents deemed and classified to be adequate and inadequate in terms of evidentiary strength for the decision-making purpose at hand.

In some situations, where topic model(s) and/or DTMs based on a reference corpus are not yet generated, step 250 comprises identifying the reference corpus having a similar context to the context determined in step 220, and then generating the topic model(s) and DTMs for the reference corpus. In particular, in some embodiments, step 240 may be applied to the reference corpus; and further, in some embodiments, step 230 (preprocessing) also may be applied to the reference corpus prior to generating the topic model(s) and DTMs.

In some embodiments, natural language processing methods are used to automatically generate topic models (step 240)— both for a reference corpus that is (for a given context and decisional usage) normative in evidentiary strength, and for each candidate document or corpus whose evidentiary adequacy is not known. Using these topic models, the linguistic perplexity and probabilistic coherence are then determined for both (step 260, below). Topics manifested in the topic model of the candidate document or corpus are matched to corresponding topics, if any, of the topic model of the reference corpus and corresponding probabilistic coherence vectors are compared (step 270, below). For example, the number of topics to be used for probabilistic coherence comparison of the candidate and reference may be less than or equal to k. The number of topics to be used for probabilistic coherence comparison of the candidate and reference may be between 4 and 20, between 5 and 15, or between 7 and 12. Further, the number of words M to be used for matching topics for the purpose of probabilistic coherence comparison may be between 4 and 20 and/or between 5 and 12.

At step 260, a probabilistic coherence is determined for each topic, and a statistical perplexity of the candidate document and reference corpus is also determined. An example of determining probabilistic coherence is provided in the example computer program routine of FIGS. 6A-6D, and an example of determining statistical perplexity is provided in the example computer program routine of FIGS. 7A-7F.

At step 270, a comparison is then performed to determine statistical differences between the candidate document and reference corpus. In an embodiment, step 270 comprises utilizing string matching to establish which topics associated with topic model(s) of the candidate document correspond to which topics associated with the topic model(s) of the reference corpus. Next a Kendall tau test, paired Wilcoxon sign-rank text, or other paired test is performed to determine statistical significance of difference candidate and reference probabilistic coherence vectors. Then a Welch t-test, Wilcoxon rank-sum, Tarone-Ware test, or other suitable test is performed to determine statistical significance of difference between candidate document and reference corpus perplexity.

In particular, statistical comparisons may be determined by any of a variety of statistically-valid tests as are suitable. However, in some embodiments, nonparametric statistical tests, such as Kendall tau test of correlation, paired Wilcoxon signed-rank test for difference between coherence vectors, permutation test, and/or Ansari test, are used as the statistical distributions are, in general, unknown—at least in the candidate documents or corpora—and are often strongly non-Gaussian. The result is a quantitative, objective determination of the evidentiary adequacy or "document quality" of the candidate document or corpus, in the same context as the reference corpus and with respect to the same decisional purposes as were applicable to the reference corpus. In an embodiment, a small amount of random noise is applied as a linear superposition to the coherence of the candidate as a means of statistically treating the possibility of "ties" between a reference and a candidate. It will be understood in the art that other statistically valid methods for treating potential ties may be incorporated without departing from the scope of the embodiments described herein.

At step 275, based on these statistical difference(s), the documentation of the candidate document is determined either to be adequate or inadequate. For example, the normative adequacy of the candidate document or corpus is ascertained by comparing the test values of probabilistic coherence of the candidate with respect to the reference corpus to an established threshold for probabilistic coherence that indicate documentation that is neither abnormally high nor abnormally low in probabilistic coherence compared to prevailing norms. Additionally, the normative adequacy of the candidate document or corpus is ascertained by comparing the test values of perplexity of the candidate with respect to the reference corpus to an established threshold for perplexity that indicate documentation that is neither abnormally high nor abnormally low in perplexity compared to prevailing norms. In some embodiments, statistical significance of difference is evaluated against a threshold, and if the threshold is satisfied, then the difference is considered significant enough to warrant notification of the candidate document as being inadequate. Otherwise, the documentation of the candidate document may be considered adequate. The threshold may be predetermined and/or may be determined based on the context of step 220. If the documentation is adequate, then at step 290, it may be noted that the document has passed review for adequacy. In some embodiments, the document may be updated to include an indicator (for instance a marking or content added to the document (such as a notification added as a footnote) or metadata associated with the candidate document) indicating that the candidate document includes adequate documentation. However, if the documentation is determined to be inadequate, then at step 280, a notification may be issued indicating that the documentation is inadequate. For example, an electronic signal may be generated indicating that the documentation is inadequate. In some embodiments, at step 280, the candidate document may be flagged or pulled for further review or for editing in order for the documentation to be adequate. The notification may be provided to a document quality manager, via manager application 140 (described in FIG. 1A) or may be provided to the creator or author of the candidate document so that that person can edit or amend the candidate document in order to make the documentation sufficiently adequate. In some embodiments the editing or amending may be facilitated by user application 142 (described in FIG. 1A). Additionally, in some embodiments, at step 280, explanatory analysis may be generated for significant values and deviations, as regards statistical normative adequacy of documentary evidence in candidate document, compared to historical reference corpus deemed to be adequate.

At step 295, it is determined whether to continue accruing or evaluating documentation for the particular case identified in step 202, or to end. If additional documentation is needed or desired, or if additional candidate documents exist to be evaluated for adequacy, then method 200 may proceed back to step 205 and another candidate document may be identified and evaluated (starting in step 210). However, if not, then method 200 ends.

Example Reductions to Practice

With reference now to FIGS. 3-7F and continuing reference to FIGS. 2, example embodiments reduced to practice are now described. Reduction to practice was accomplished using a computer running the Linux operating system (operating system 129), the open-source statistical software package R (computation services 126), and in particular using the example computer program routines illustratively provided in FIGS. 6A-6D and 7A-7F.

For the reduction to practice, an observational study of was performed on de-identified, HIPAA-compliant electronic health record (EHR) documentation accruing during the care of (a) 1,267 subjects for ECG-established non-ST-elevated myocardial infarction (NSTEMI) between 1 Jan. 2015 and 31Dec.-2015 (an example of which is shown in FIG. 4) and (b) 348 in-patient subjects with laboratory culture-documented central line-associated blood stream infection (CLABSI) incidented within the same time interval (an example of which is shown in FIG. 5).

Figure 3:
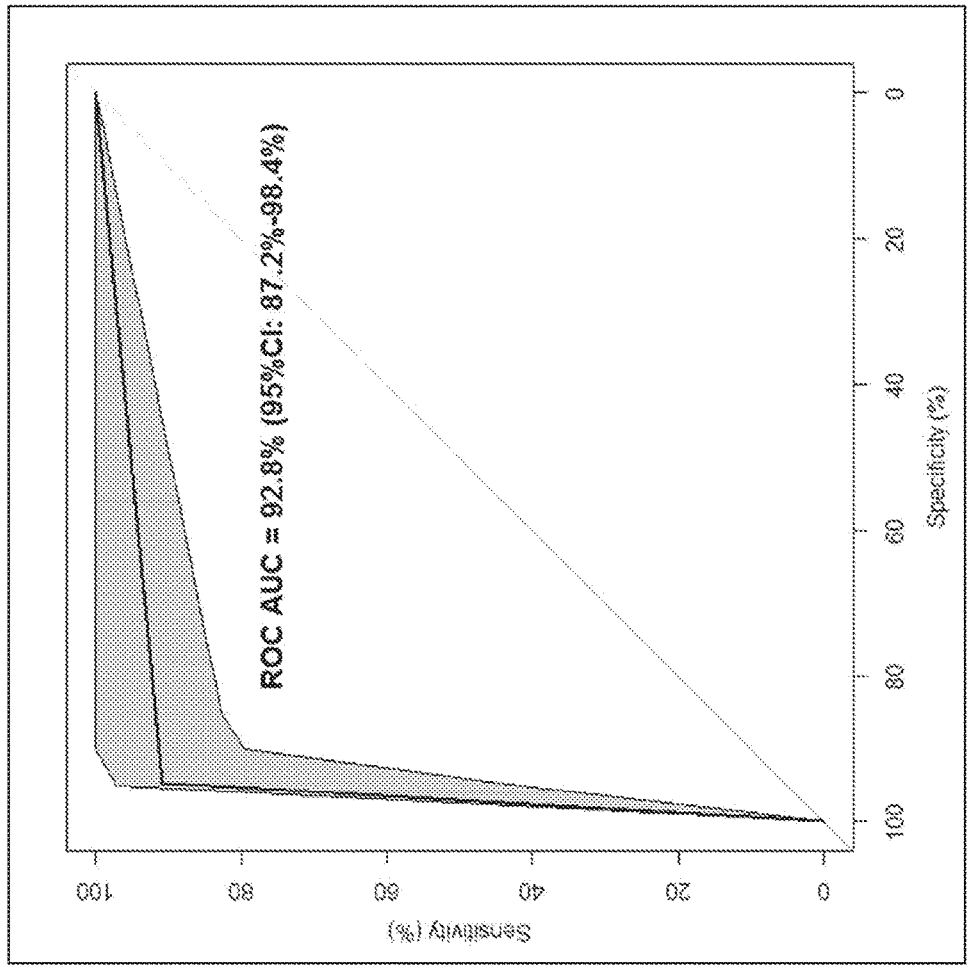
FIG. 3 depicts aspects of an example embodiment actually reduced to practice for predicting risk for non-adherence, including a receiver operating characteristic (ROC) curve.

In these examples, using an embodiment of method 200, LDA topic models were generated via computation services 126 including R-system packages lda, textmineR, tm, text2vec, SnowballC, NLP, and topicmodels, as shown in the example computer program of FIGS. 7A-7F. The computer program routines shown in FIGS. 6A-6D and 7A-7F were utilized for determining probabilistic coherence (FIGS. 6A-6D) and statistical perplexity (FIGS. 7A-7F). FIG. 3 shows a receiver operating characteristic (ROC) curve of the statistical classificatory performance of one embodiment of the invention as applied to these two health services documentation corpora. An AUC of 92.8% at a confidence interval of 95% is shown, which represents a significant improvement over the prior art technologies.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and sub-combinations are of utility and may be employed without reference to other features and sub-combinations and are contemplated within the scope of the claims. Not all steps listed in the various figures need be carried out in the specific order described. Accordingly, the scope of the invention is intended to be limited only by the following claims.

What is claimed is:

1. A computer readable media having computer-executable instruction stored thereon for automatically identifying deficiencies in narrative textual data based on a determined statistical perplexity and probabilistic coherence which, when executed by at least one processor, perform operations comprising:
   connect to a server with access to a candidate corpus of text;
   monitor signals generated by the server in response to the server's evaluation of the candidate corpus of text to identify deviations of the candidate corpus of text from a reference corpus using a topic model generated using at least one reference corpus of text defined as epistemically persuasive and adequate for a decision-making purpose,
   wherein the evaluation of the candidate corpus of text comprises accessing a set of stopwords and related linguistic parameters associated with the decision-making purpose, and computing a degree to which a statistical perplexity and a probabilistic coherence of the candidate corpus of text deviate from reference corpus based on the set of stopwords and related linguistic parameters; and
   responsive to a signal indicating that the evaluation of the candidate corpus of text exceeds a predetermined limit based on the statistical perplexity or the probabilistic coherence, generate a notification to a user.

2. The computer readable media of claim 1, wherein the topic model is a latent Dirichlet allocation (LDA) or a correlated-topics model (CTM).

3. The computer readable media of claim 2, wherein the topic model comprises an alpha parameter in between 0.05 and 0.90, between 0.10 and 0.25, or between 0.01 and 0.99.

4. The computer readable media of claim 1, wherein the topic model is generated by Gibbs sampling or variational expectation-maximization (VEM) algorithm.

5. The computer readable media of claim 1, wherein the operations further comprise conditioning the candidate corpus by removing stopwords and word-stemming from the text of the candidate corpus.

6. The computer readable media of claim 1, wherein the notification prompts the user for additional review or an amendment of the candidate corpus before records associated with the candidate corpus are submitted.

7. The computer readable media of claim 1, wherein the probabilistic coherence of the candidate corpus is determined with respect to the reference corpus by a Kendall tau test, a paired Wilcoxon sign-rank test, a permutation test, or a Ansari test.

8. A system for automatic identification of deficiencies in narrative textual data, the system comprising:
   one or more processors;
   computer memory having computer executable instructions stored thereon that when executed by the one or more processors cause the one or more processors to perform operations including:
   connect to a health record system with access to a candidate corpus of text;
   capture signals that are generated by the health record system in response to the health record system's evaluation of the candidate corpus of text, the evaluation identifying deviations of the candidate corpus of text from a reference corpus using a topic model generated using at least one reference corpus of text defined as epistemically persuasive and adequate for a decision-making purpose, wherein the evaluation of the candidate corpus of text comprises accessing a set of stopwords and related linguistic parameters associated with the decision-making purpose, and computing a degree to which a statistical perplexity and a probabilistic coherence of the candidate corpus of text deviate from reference corpus based on the set of stopwords and related linguistic parameters; and responsive to a signal indicating that the evaluation of the candidate corpus of text does not exceed a predetermined limit based on the statistical perplexity or probabilistic coherence, generate a notification to a user.

9. The system of claim 8, wherein the topic model is a latent Dirichlet allocation (LDA) or a correlated-topics model (CTM).

10. The system of claim 8, wherein the topic model is generated by Gibbs sampling or variational expectation-maximization (VEM) algorithm.

11. The system of claim 8, wherein the computer-executable instructions further cause the one or more processors to condition the candidate corpus but removing stopwords and word-stemming from the text of the candidate corpus.

12. The system of claim 8, wherein the notification prompts the user for additional review and amendment before records associated with the candidate corpus are submitted.

13. The system of claim 8, wherein the probabilistic coherence of the candidate corpus is determined with respect to the reference corpus by a Kendall tau test, a paired Wilcoxon sign-rank test, a permutation test, or a Ansari test.

14. A method for automatically identifying deficiencies in narrative textual data, the method comprising:
  connecting to a health record system with access to a candidate corpus of text;
  monitoring signals that are generated by the health record system in response to the health record system's evaluation of the candidate corpus of text, the evaluation identifying deviations of the candidate corpus of text from a reference corpus using a topic model generated using at least one reference corpus of text defined as epistemically persuasive and adequate for a decision-making purpose,
  wherein the evaluation of the candidate corpus of text comprises accessing a set of stopwords and related linguistic parameters associated with the decision-making purpose, and computing a degree to which a statistical perplexity and a probabilistic coherence of the candidate corpus of text deviate from reference corpus based on the set of stopwords and related linguistic parameters; and
  responsive to a signal indicating that the evaluation of the candidate corpus of text does not exceed a predetermined limit based on the statistical perplexity or probabilistic coherence, generating a notification to a user.

15. The method of claim 14, wherein the topic model is a latent Dirichlet allocation (LDA) or a correlated-topics model (CTM).

16. The method of claim 14, wherein the topic model comprises an alpha parameter in between 0.05 and 0.90, between 0.10 and 0.25, or between 0.01 and 0.99.

17. The method of claim 14, wherein the topic model is generated by Gibbs sampling or variational expectation-maximization (VEM) algorithm.

18. The method of claim 14, further comprising conditioning the candidate corpus by removing stopwords and word-stemming from the text of the candidate corpus.

19. The method of claim 14, wherein the topic model is configured for determining a statistical perplexity and probabilistic coherence when applied to a corpus of text.

20. The method of claim 14, wherein the probabilistic coherence of the candidate corpus is determined with respect to the reference corpus by a Kendall tau test, a paired Wilcoxon sign-rank test, a permutation test, or a Ansari test.

* * * * *